US012633435B2

(12) United States Patent　　　(10) Patent No.: US 12,633,435 B2
Pellegrino et al.　　　　　　　　　(45) Date of Patent: May 19, 2026

(54) METHOD FOR THE GRAM-SCALE PREPARATION OF FERRITE NANOPARTICLES FOR MAGNETIC HYPERTHERMIA APPLICATIONS

(71) Applicant: FONDAZIONE ISTITUTO ITALIANO DI TECNOLOGIA, Genoa (IT)

(72) Inventors: Teresa Pellegrino, Genoa (IT); Helena Gavilan Rubio, Genoa (IT); Giusy Maria Rita Rizzo, Genoa (IT); Niccolò Silvestri, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 448 days.

(21) Appl. No.: 18/250,812

(22) PCT Filed: Oct. 27, 2021

(86) PCT No.: PCT/EP2021/079835
§ 371 (c)(1),
(2) Date: Apr. 27, 2023

(87) PCT Pub. No.: WO2022/090316
PCT Pub. Date: May 5, 2022

(65) Prior Publication Data
US 2023/0402209 A1　　Dec. 14, 2023

(30) Foreign Application Priority Data

Oct. 29, 2020　　(IT) ........................ 102020000025738

(51) Int. Cl.
H01F 1/00　　　　(2006.01)
A61K 41/00　　　(2020.01)
(Continued)

(52) U.S. Cl.
CPC ....... H01F 1/0054 (2013.01); A61K 41/0052 (2013.01); C01G 49/08 (2013.01);
(Continued)

(58) Field of Classification Search
CPC .................................................. A61K 41/0052
See application file for complete search history.

(56) References Cited

U.S. PATENT DOCUMENTS

2022/0227639 A1　　7/2022　Pellegrino et al.

FOREIGN PATENT DOCUMENTS

CN　　　105999266 A　　10/2016
JP　　　2009233845 A　　10/2009
(Continued)

OTHER PUBLICATIONS

International Search Report for International Patent Application No. PCT/EP2021/079835, mailed Nov. 22, 2021.
(Continued)

*Primary Examiner* — Benjamin J Packard
(74) *Attorney, Agent, or Firm* — Armstrong Teasdale LLP

(57)　　　　　ABSTRACT

A method for preparing ferrite nanoparticles employing as directing agent an aldehyde or ketone of formula $R_1$—$(C{=}O)R_2$ is provided. $R_1$ is a linear or branched, saturated or unsaturated carbon chain having a length between 1 and 13 carbon atoms, optionally substituted with an aromatic substituent. $R_2$ is selected from the group consisting of hydrogen, an aromatic ring and a linear or branched, saturated or unsaturated carbon chain having a length between 1 and 10 carbon atoms. When $R_2$ is hydrogen and $R_1$ is an unsaturated carbon chain substituted with an aromatic substituent, the aromatic substituent is located at position 3 or higher with respect to the carbonyl group —$(C{=}O)$. When $R_2$ is hydrogen and $R_1$ is a saturated carbon chain substituted with an aromatic substituent, the aromatic substituent is (Continued)

Alcohol
Amine
Oleic acid

30' at 60 °C
Magnetic stirring (800 rpm)

Homogeneous solution

Cool down to RT

Organometallic precursor and Aldehyde* or Ketone** in the alcohol solution

20' at RT
Magnetic stirring (800 rpm)

Seal in the reaction vessel (filled to a 20-70% in volume)

Heating in the oven for 3-8 h at 180-240 °C

Washing with acetone

20', 4500 rpm

NANOPARTICLES OF Fe₃O₄

*Heptanal or pentanal or decanal, etc.
**Methyl phenyl ketone or diphenyl ketone, etc.

located at position 2 or higher with respect to the carbonyl group —(C=O). When the aromatic substituent is located at position 2, the aromatic substituent is the sole substituent at position 2.

13 Claims, 8 Drawing Sheets

(51) Int. Cl.

| | |
|---|---|
| *C01G 49/08* | (2006.01) |
| *B82Y 5/00* | (2011.01) |
| *B82Y 30/00* | (2011.01) |
| *B82Y 40/00* | (2011.01) |

(52) U.S. Cl.
CPC ................. *B82Y 5/00* (2013.01); *B82Y 30/00* (2013.01); *B82Y 40/00* (2013.01)

(56) References Cited

FOREIGN PATENT DOCUMENTS

| | | |
|---|---|---|
| WO | 2010062127 A2 | 6/2010 |
| WO | 2013150496 A1 | 10/2013 |

OTHER PUBLICATIONS

Roca, A.G. et al., Design strategies for shape-controlled magnetic iron oxide nanoparticles, Advanced Drug Delivery Reviews, Jan. 1, 2019, pp. 68-104, vol. 138, Elsevier B.V.

Das R. et al., Tunable High Aspect Ratio Iron Oxide Nanorods for Enhanced Hyperthermia, The Journal of Physical Chemistry C, May 12, 2016, pp. 10086-10093, vol. 120, Issue 18, American Chemical Society.

Kotoulas A. et al., The Effect of Polyol Composition on the Structural and Magnetic Properties of Magnetite Nanoparticles for Magnetic Particle Hyperthermia, Materials, published Aug. 21, 2019, 2663, vol. 12, Issue 17, MDPI, Basel, CH.

Fotukian S. M. et al., Solvothermal synthesis of CuFe2O4 and Fe3O4 nanoparticles with high heating efficiency for magnetic hyperthermia application, Journal of Alloys and Compounds, Mar. 5, 2020, 152548, vol. 816, Elsevier B.V.

Lartigue L. et al., Cooperative Organization in Iron Oxide Multi-Core Nanoparticles Potentiates Their Efficiency as Heating Mediators and MRI Contrast Agents, ACS Nano, 2012, pp. 10935-10949, vol. 6, No. 12, ACS Publications.

Caruntu D. et al., Synthesis of Variable-Sized Nanocrystals of Fe3O4 with High Surface Reactivity, Chemistry of Materials, published Nov. 11, 2004, pp. 5527-5534, vol. 16, Issue 25, ACS Publications.

Salas G. et al., Controlled synthesis of uniform magnetitenanocrystals with high-quality properties for biomedical applications, Journal of Materials Chemistry, 2012, Issue 39, The Royal Society of Chemistry, GB.

Darwish M. et al., Synthesis of Magnetic Ferrite Nanoparticles with High Hyperthermia Performance via a Controlled Co-Precipitation Method, Nanomaterials, 1176, vol. 9, Issue 8, MDPI, Basel, CH.

Guardia P. et al., Controlled Synthesis of Iron Oxide Nanoparticles over a Wide Size Range, Langmuir, Apr. 20, 2010, pp. 5843-5847, vol. 26, Issue 8, ACS Publications.

Mehdaoui B. et al., Optimal Size of Nanoparticles for Magnetic Hyperthermia: A Combined Theoretical and Experimental Study, Advanced Functional Materials, Dec. 6, 2011, pp. 4573-4581, vol. 21, Issue 23, Wiley-VCH Verlag GmbH, DE.

*Heptanal or pentanal or decanal, etc.
**Methyl phenyl ketone or diphenyl ketone, etc.

Trans-1-phenyl-2-buten-one

Methyl Phenyl Ketone

Diphenyl Ketone

Figure 4

| Shape | | Size (nm) | Frequency (kHz) | Amplitude (kA/m) | Hf * 10⁹ (A/ms) | SAR (W/gFe) |
|---|---|---|---|---|---|---|
| Spherical | Thermal dec. (G. Salas et al.) | 12±1 | 77 | 39 | 3 | 17 |
| Spherical | Our solvothermal method | 17±2 | 100 | 24 | 2,4 | 25 |
| Spherical | Thermal dec. (G. Salas et al.) | 18±4 | 77 | 39 | 3 | 35 |
| Nanofaceted | Thermal dec. (G. Salas et al.) | 14±1 | 77 | 32 | 2,4 | 50 |
| Nanofaceted | Our solvothermal method | 14±1 | 100 | 24 | 2,4 | 100 |
| Nanofaceted | Thermal dec. (G. Salas et al.) | 18±2 | 77 | 32 | 2,4 | 90 |
| Nanofaceted | Our solvothermal method | 18±2 | 100 | 24 | 2,4 | 200 |
| Nanofaceted | Thermal dec. (G. Salas et al.) | 22±2 | 77 | 32 | 2,4 | 200 |
| Nanofaceted | Our solvothermal method | 20±3 | 100 | 24 | 2,4 | 475 |
| Resovist | Co-precipitation (Darwish, M. et al.) | xx | 105 | 40 | 4,2 | 24 |

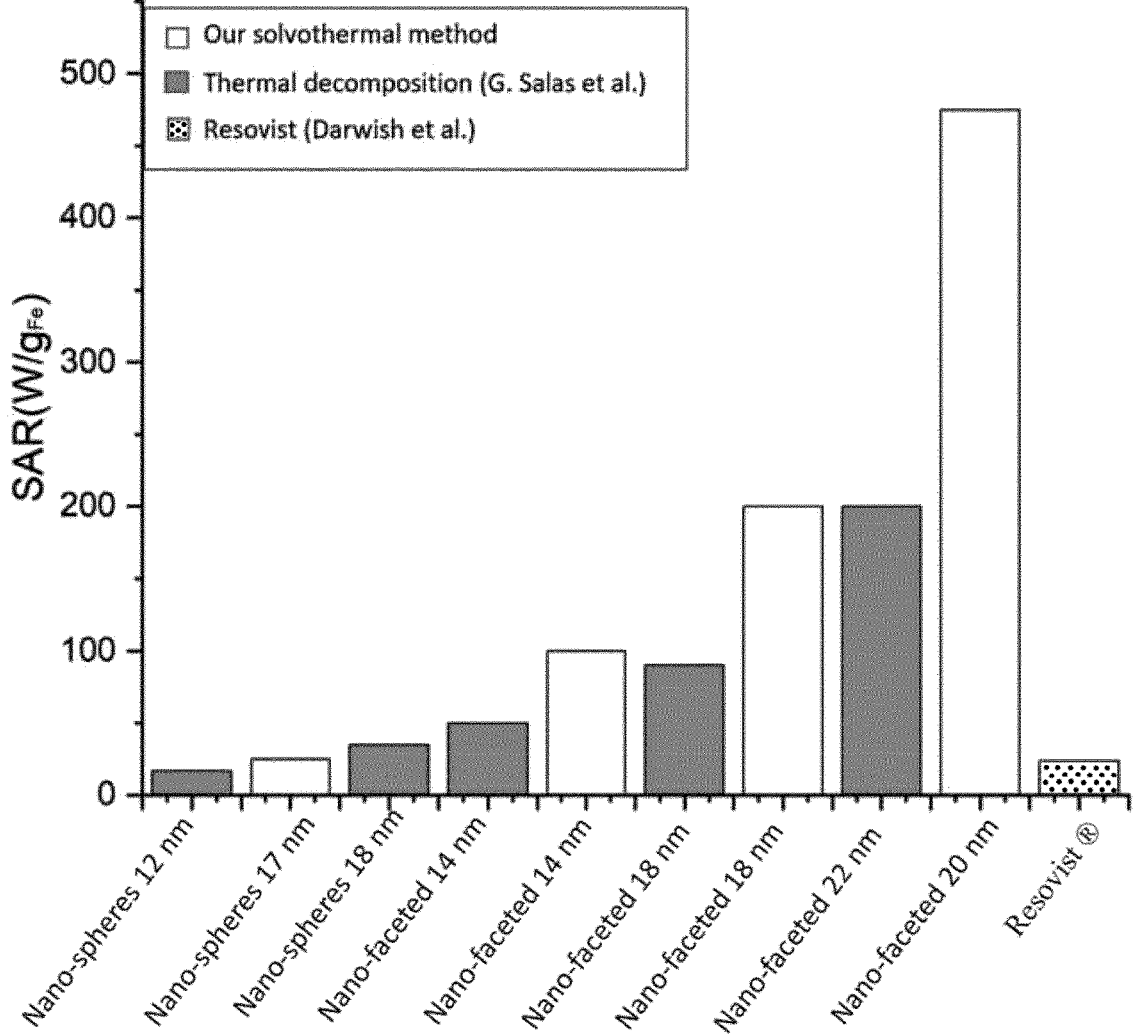

FIG.8

METHOD FOR THE GRAM-SCALE PREPARATION OF FERRITE NANOPARTICLES FOR MAGNETIC HYPERTHERMIA APPLICATIONS

CROSS-REFERENCE TO RELATED APPLICATIONS

This application is a National Stage Application of International Patent Application No. PCT/EP2021/079835, having an International Filing Date of Oct. 27, 2021, which claims priority to Italian Application No. 102020000025738 filed Oct. 29, 2020, the entire contents of each of which are hereby incorporated by reference herein.

TECHNICAL FILED

The present invention relates to a method for preparing magnetic nanoparticles having controlled structural and magnetic properties for biomedical applications, in particular for the application thereof as thermal mediators in magnetic hyperthermia.

PRIOR ART

In the area of nanomedicine, the use of magnetic nanoparticles (MNPs) plays an important role, thanks to their magnetic properties, i.e. they can be introduced in the body to carry drugs, they can be monitored under different magnetic fields and they can produce heat when exposed to alternating (AC) magnetic field. Magnetic hyperthermia is the generation of heat by magnetic nanoparticles when exposed to an alternating magnetic field. The temperature increase to a therapeutic value of 45° C. is used to treat cancer in a selective manner, upon accumulation of MNPs at the tumor site. For MH (magnetic hypertermia) application it is important to evaluate the specific absorption rate (SAR) values that MNPs display, which is a physical magnitude related to the heat dissipation of MNPs when exposing to the AC field.

A major challenge in the last years has been to increase the heating efficiency (SAR values) of MNPs. Several studies demonstrated the possibility to significantly improve the heating efficiency by tuning the crystallinity, shape, size and size distribution of MNPs thus applying less dose of MNPs in MH treatment.

The MNPs used in clinics are composed of iron oxide nanoparticles of spherical shape (with a chemical composition of magnetite/$Fe_3O_4$ and maghemite/$\gamma$-$Fe_2O_3$), which are commonly produced by co-precipitation method. This is a simple and low-cost method enabling the production gram scale production of MNPs. However, MNPs produced by this route have poor quality in terms of size distribution (frequently the standard deviation is above 20%), poor morphology control and low crystallinity, which is reflected in poor saturation magnetization ($M_s$) values (4-11 nm MNPs have values of $M_s$ of 40-70 emug$^{-1}$ at room temperature) and, in turn, poor SAR values (for a size range 8-20 nm SAR values correspond to 10-52 Wg$^{-1}$) similar to those of commercially available sample of MNPs Resovist®. Size selection protocol can be used to reduce the size distribution. However this protocol is time consuming and reduces the amount of the magnetic materials that can be obtained.

On the other hand, the synthesis route of high temperature thermal decomposition has demonstrated to offer a control over both the size, size distribution, shape and crystallinity of MNPs, displaying higher values of $M_s$ and SAR. In order to control the size and shape of MNPs, thermal decomposition route uses capping agents (i.e. surfactants, stabilizers, adsorbates, or polymers) having functional groups that coordinate metal cations and hydrophobic carbon chain that allow the solubility of the metal chemical species in solution, controlling the nucleation and the growth of the crystal along well-defined crystallographic directions thus enabling to tune the shape of the MNPs. Some examples of typical ligands used for high-temperature decomposition of organic precursors are the carboxylic acids (oleic acid, decanoic acid), the amines (oleylamine, dodecylamine) and the phosphines (TOP, TOPO). With respect to the SAR values, faceted $Fe_3O_4$ nanoparticles (6-12 nm) showed SAR values from 163 to 275 W·g$^{-1}$ (247 kHz, 310 Oe). By increasing the size of the faceted MNPs (40 nm), SAR values were maintained 157 W·g$^{-1}$(358 kHz, 200 Oe) or increased up to 2483 W·g$^{-1}$, if the field amplitudes of the applied AC field were stronger (358 KHz, 800 Oe). (Roca, A. G., et al. Advanced Drug Delivery Reviews) However, the latter field condition is not suitable for the biomedical application of MNPs because an H×f product as high as 2.3×10$^{10}$ A/ms would generate non-specific Eddy currents in patients (in general, a frequency of 110 kHz and an intensity of between 10 and 24 kAm$^{-1}$ are used on patients). The major disadvantage of high-temperature thermal decomposition synthesis route is, however, that the amount of nanoparticles produced per batch that is definitively lower (in the scale of milligrams or tens of milligrams) than chemical co-precipitation method and the overall complexity of the process (the need of magnetic/mechanical stirring system, an inert gas flow during the process, temperatures well above 250° C., complex temperature ramps, etc.) makes the synthesis expensive and costly.

The typical dose of spherical nanoparticles required for magnetic hyperthermia treatment of a patient is 7-12 mL of a solution containing 100-120 mg Fe/mL, therefore having magnetic nanoparticles with higher SAR values than those used in clinic, would make it possible to considerably reduce the dose to be administered to each patient during the treatment.

Solvothermal methods for preparing nanoparticles for MH have recently been proposed in literature. In particular, Raja Das et al. in "Tunable High Aspect Ratio Iron Oxide Nanorods for Enhanced Hyerthermia," published in J. Phys. Chem. C 2016 120, 10086-10093, report the synthesis of nanorods of $Fe_3O_4$ from an organometallic precursor, a surfactant and an organic base in the presence of 1-octanol as the solvent, after 6 hours at 200° C. in an autoclave.

However, the authors reported very poor SAR values when considered MH conditions safe for the clinics (40 Wg$^{-1}$ for a Hf of 5×10$^9$ Am$^{-1}$s$^{-1}$), getting values very similar as those of Resovist®. Kotoulas, A. et al. reported the synthesis of quasi spherical nanoparticles of 4-12 nm using triethylene glycol as solvent, iron (III) acetylacetonate as iron source, polyethylene glycol as surfactant and hydrazine as base. However, the authors reported very poor SAR values for MH conditions that were unsafe for the clinics (25-200 Wg$^{-1}$ for a H of 12 kA/m and a f of 765 kHz with an H×f of 9,2×10$^9$ Am$^{-1}$s$^{-1}$). S. M. Fotukian et al reported a solvothermal method also using triethylene glycol as solvent, iron (III) acetylacetonate as iron source, however the authors likewise reported very poor SAR values (below 20 Wg$^{-1}$ for a Hf of 2.3×10$^9$ Am$^{-1}$s$^{-1}$) for spherical nanoparticles of 9 nm (Journal of Alloys and Compounds, 2020, vol. 816, p. 152548.). Finally, Lartigue et al. reported improved SAR values for iron oxide nano-flowers, obtained by modifying the solvothermal method developed by Caruntu et al. (Chemistry of materials. 2004; 16(25):5527-34) in "Synthesis of variable-sized nanocrystals of $Fe_3O_4$ with high surface reactivity". In this synthesis, diethylene glycol was used as the solvent, the iron precursors were a mixture of FeCl2 and FeCl3 and a mixture of bases (N-Methyldiethanolamine and NaOH) was used. The MNPs produced were transferred to water using an acid treatment and after a size-sorting process, the resulting nano-flowers fractions reached values of SAR of 500 $Wg^{-1}$ for a Hf of $4.4 \times 10^9$ $Am^{-1}s^{-1}$ (nanoparticle's diameter was 21 nm) (Lartigue L, at al. ACS Nano. 2012; 6(12):10935-49).

However, none of the methods cited above makes it possible to obtain a good yield of magnetic nanoparticles having a high specific absorption rate and in a manner that may be implemented on a large scale. In the field of magnetic hyperthermia, there is therefore still an urgent need to provide methods for preparing magnetic nanoparticles having optimum magnetic and colloidal properties for clinical application, which methods are easy to implement on a large scale.

Therefore, there is still an urgent need of scalable processes for the production of MNPs with controlled size and shape and with elevated SAR values, suitable for MH treatment of cancer. In Italian patent application IT 102019000006469, the inventors disclosed a method for preparing ferrite nanoparticles of cubic-like shape, comprising the following steps:

i) providing a solution comprising a fatty acid, an aliphatic amine and an alcoholic solvent;

ii) adding at least one organometallic precursor compound comprising Fe and optionally a second organometallic precursor compound comprising a metal selected from Mn, Co, Zn and an aromatic organic molecule to the solution in point i) thereby obtaining a reaction mixture;

iii) transferring the reaction mixture obtained in step ii) to a sealed reactor, thereby obtaining a filling percentage thereof of between 20 and 70 vol. %; and iv) heating said sealed reactor to a temperature of between 160° C. and 240° C. for at least 3 hours.

The aromatic organic molecule used in IT 102019000006469 is preferably an aromatic aldehyde, such as for example benzaldehyde, 4-biphenyl carbaldehyde, 2-phenylpropionaldehyde, 1,4-benzenedicarboxaldehyde, 4-methylbenzaldehyde, vinylbenzaldehyde, isopropenyl-benzenaldehyde, 4-isopropylbenzaldehyde, 4-(1-methyl-ethyl)benzaldehyde. The aromatic aldehyde disclosed in IT 102019000006469 is a "directing agent", i.e. a compound that is able to influence the growth of a nanoparticle to assume a predefined shape. The aromatic organic molecules exemplified in IT 102019000006469 are able to direct the reaction towards the synthesis of cubic ferrite nanoparticles with particularly elevated SAR ("specific absorption rate") values, elevated colloidal stability, substantially regular cubic shape and controlled dimensions, which make them particularly suitable for the clinical use in magnetic hyperthermia.

SUMMARY OF THE INVENTION

The inventors have now found that, by using alternative aldehyde and/or ketone directing agents which are not specifically disclosed in IT 102019000006469, it is possible to obtain ferrite nanoparticles having shapes different from the cubic-like shape disclosed in IT 102019000006469, such as for example faceted or spherical shapes, but which still show elevated SAR ("specific absorption rate") values which make them suitable for use in magnetic hyperthermia applications.

The synthesis method of the present invention provides, in a scaled-up manner, ferrite nanoparticles having controlled size (in the range of about 9-20 nm), shapes and crystallinity and showing outstanding heating performances.

Accordingly, the present invention relates to a method for preparing magnetic nanoparticles, which has the features defined in the appended claims.

Additional advantages and features of the method of the invention will become clear from the following description regarding both the general method features and specific embodiments thereof.

BRIEF DESCRIPTION OF THE DRAWINGS

In the attached drawings:

FIG. 4 shows the TEM images of MNPs obtained using different examples of ketones of Formula (I), i.e.: a)trans-1-phenyl-2-buten-one, b)methyl phenyl ketone, c) diphenyl ketone.

FIG. 8 shows SAR values (in table and on graph) at comparable H, f and H×f factors for the nano-spheres and nano-faceted obtained with the solvothermal method of the present invention, with those of similar size and morphology produced by thermal decomposition methods accordingly to literature reported protocols (G. Salas et al. J. Mater. Chem, 2012, vol. 22, no 39, p. 21065-21075). For comparison the SAR value for the commercially available product, Resovist® at the same Hf value (Darwish, M. et al., Nanomaterials 9.8 (2019): 1176) is also reported.

DETAILED DESCRIPTION OF THE INVENTION

Figure 1:
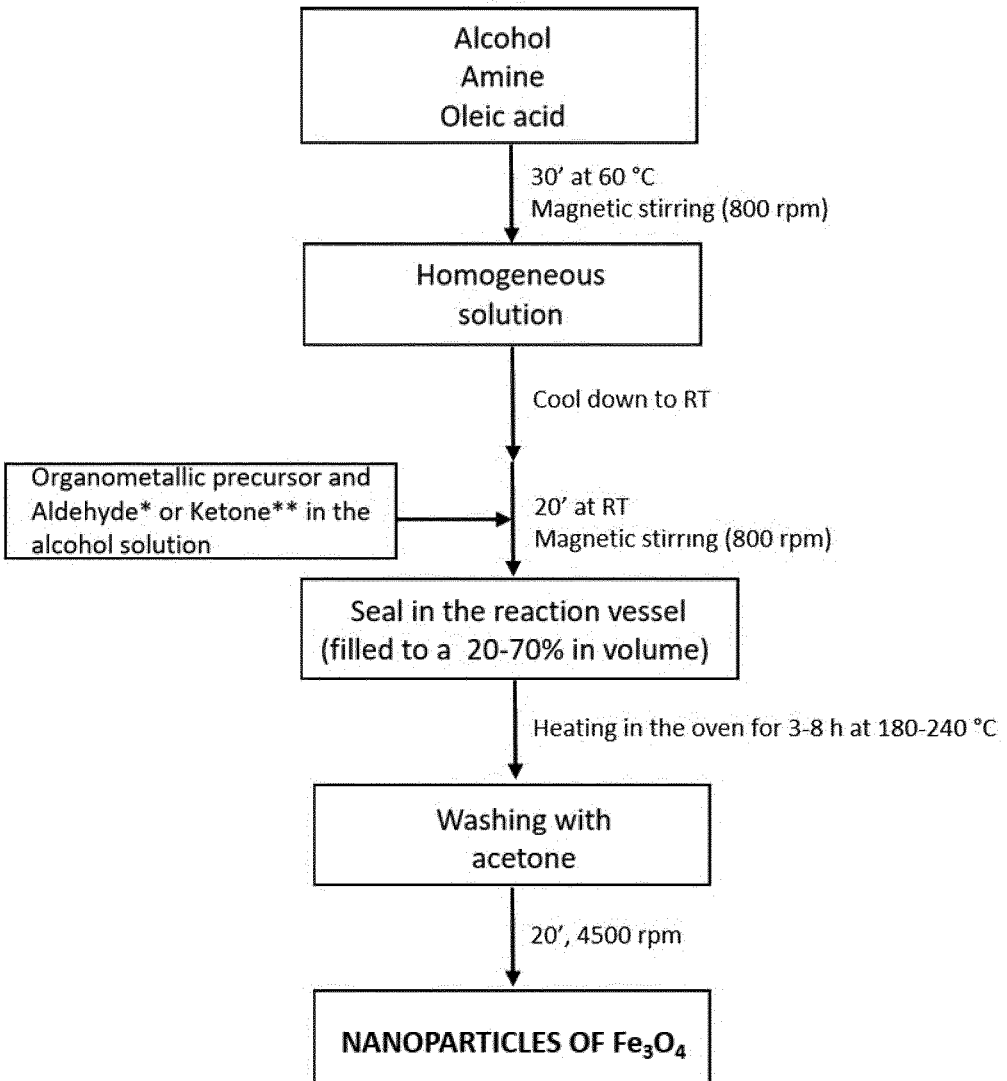
FIG. 1 is the block diagram of the synthesis method used in Example 1.

For the purposes of the present description, the following terms are understood as having the following meanings.

"Directing agent" indicates a compound that is able to influence the growth of a nanoparticle to assume a pre-defined shape. Examples of common directing agents are polymers, surfactants, ionic salts and organic molecules.

"Precursor" indicates a chemical species containing at least one of the metal elements necessary for the nucleation/growth of the ferrite nanoparticles.

"Ligand" indicates a chemical species having surfactant properties that are able to coordinate the metal precursors and the nuclei and growing crystals.

"Ferrite" indicates a chemical compound consisting of a mixture of iron oxides and optionally oxides of other metals selected from Fe, Mn, Co and Zn, having a high degree of magnetic permeability.

Water transfer agents are molecules or polymers able to coordinate to the as obtained nanoparticles and allow their transfer to water. Preferentially they can be Polyethylene glycol and its derivatives, tetramethylammonium hydroxide, amphiphilic polymers, dextran, or sucrose molecules.

In a first aspect, the present invention relates to a method for producing ferrite nanoparticles, comprising the following steps:

i) providing a solution comprising a fatty acid, an aliphatic amine and an alcoholic solvent;

ii) adding to the solution in step i) a directing agent and at least one organometallic precursor compound comprising Fe and optionally a second organometallic precursor compound comprising a metal selected from Mn, Co, Zn, and, thereby obtaining a reaction mixture;

iii) transferring the reaction mixture obtained in step ii) to a sealed reactor, thereby obtaining a filling percentage thereof of between 20 and 70 vol. %; and iv) heating said sealed reactor to a temperature of between 160° C. and 240° C. for at least 3 hours, characterized in that the directing agent is an aldehyde or ketone of Formula (I):

$$R_1—(C═O)R_2 \hspace{4em} \text{Formula (I)}$$

wherein $R_i$ is a linear or branched, saturated or unsaturated carbon chain having a length of from 1 to 13 carbon atoms, optionally substituted with an aromatic substituent, and $R_2$ is selected from the group consisting of hydrogen, an aromatic ring and a linear or branched, saturated or unsaturated carbon chain having a length of from 1 to 10 carbon atoms, with the provisos that:

(i) when $R_2$ is hydrogen and $R_1$ is a an unsaturated carbon chain substituted with an aromatic substituent, the aromatic substituent is located at position 3 or higher with respect to the carbonyl group —(C═O), or (ii) when $R_2$ is a hydrogen and $R_1$ is a saturated carbon chain substituted with an aromatic substituent, the aromatic substituent is located at position 2 or higher with respect to the carbonyl group —(C═O), with the further proviso that when the aromatic substituent is located at position 2, the aromatic substituent is the sole substituent at position 2.

The aforementioned definition for $R_1$ includes carbon chains having a length of 1, 2, 3, 4, 5, 6, 7, 8, 9, 10, 11, 12 and 13 carbon atoms.

The aforementioned definition for $R_2$ includes carbon chains having a length of 1, 2, 3, 4, 5, 6, 7, 8, 9 and 10 carbon atoms.

A preferred aromatic substituent in the definition of both $R_1$ and $R_2$ is a phenyl group optionally bearing one or more substituents.

A preferred length for the $R_1$ carbon chain is of from 1 to 11 carbon atoms.

A preferred length for the $R_2$ carbon chain is of from 1 to 5 carbon atoms.

In the method of the invention, in order to prepare the solution in step i), the components may be added under magnetic agitation and heating in order to facilitate the dissolution thereof and the attainment of a homogenous solution.

Said fatty acid is preferably a saturated or unsaturated fatty acid having an aliphatic chain having between 10 and 18 carbon atoms. In a particularly preferred embodiment, said fatty acid is selected from oleic acid and decanoic acid.

Said aliphatic amine may be a primary, secondary or tertiary amine. Said aliphatic amine preferably has an alkyl chain having between 8 and 18 carbon atoms. Even more preferably, said aliphatic amine is hexadecylamine.

Said alcoholic solvent is selected from linear alcohols having an alkyl chain of between 2 and 8 carbon atoms and benzyl alcohol. In a particularly preferred embodiment, said alcohols are selected from 1-butanol and 1-octanol.

In step ii), the components may be added in the presence of magnetic agitation and at a temperature of between room temperature and the dissolution temperature used in step i).

In a particularly preferred embodiment, said organometallic precursor compound is selected from iron pentacarbonyl of formula Fe(CO)s, zinc acetylacetonate of formula $Zn(AcAc)_2$, cobalt(II) acetylacetonate of formula $Co(AcAc)_2$, manganese acetylacetonate of formula $Mn(AcAc)_2$, and mixtures thereof.

As shown in Formula (I), the directing agent employed in the present invention is either an aliphatic aldehyde, or an aromatic aldehyde or ketone. Illustrative, non-limiting examples of directing agents employed in the method of the invention are pentanal, heptanal, decanal, 3-phenylpropanal, 2-phenylacetaldehyde, (Z)-hept-4-enal, (E)-3-phenylprop-2-enal, trans-1-phenyl-2-buten-one, methyl phenyl ketone, diphenyl ketone.

In the embodiments in which said organic molecule is in the solid state at room temperature and pressure, it may be added to step i) to facilitate the dissolution thereof in the reaction mixture.

Optionally, the above-mentioned organic aldehydes or ketones of Formula (I) may be used in admixture with one or more other directing agents, such as alkylamines or trioctylphosphine (TOPO).

In step iii), said sealed reactor is preferably a Teflon-lined autoclave (for operating temperatures of up to 200° C.), or p-polyphenylene (PPL) (for temperatures above 200° C.).

Alternatively, any reactors on the market may be used that may be sealed and pressurized, for example Parr® reactors. The use of a sealed reactor makes it possible to obtain an autogenous pressure inside said reactor and this pressure ensures the high degree of crystallinity of the end product, despite the reduced operating temperature. Extensive studies have made it possible to determine the importance of parameters such as the reactor volume and the filling percentage thereof on the end properties of the ferrite nanoparticles, as shown in Example 2. The average diameter of the nanoparticles can be increased by tuning simultaneously two experimental conditions: increasing the filling percentage of the autoclave (from 20 to 70% in volume) and increasing the annealing temperature at the furnace (from 180 to 240° C.). (FIG. 2b-c are some examples). The monodispersity of the nanoparticles is not influenced despite changing such experimental conditions.

Figure 2:
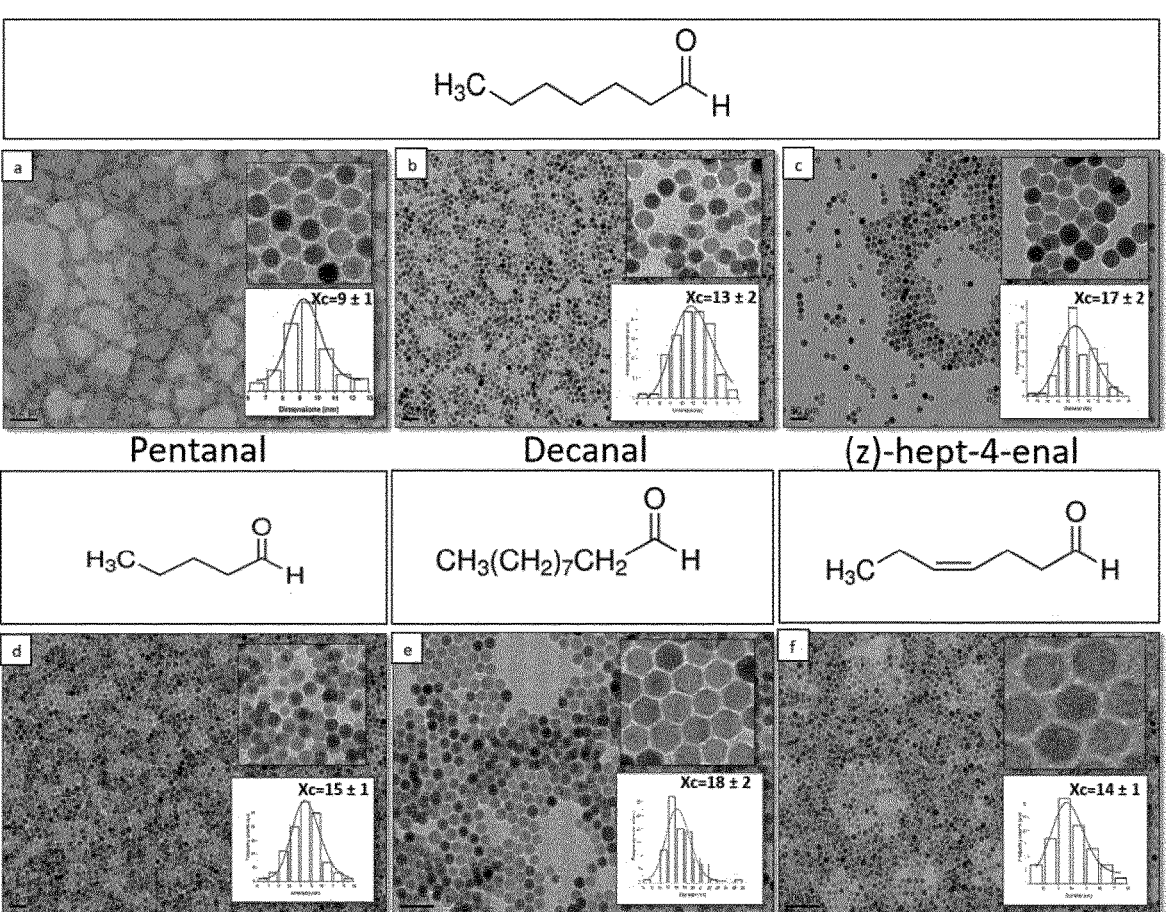
FIG. 2 shows the TEM images and the size distribution analysis of MNPs obtained using different aliphatic aldehydes of Formula (I) as the directing agent, i.e.: a-c) heptanal, d) pentanal, e) decanal, f) (z)-hept-4-enal.

For instance in the specific case of Example 2, increasing the temperature of the furnace from 200 to 220° C. and the filling percentage of the autoclave from 46 to 60% in volume, it is possible to increase the average diameter of the MNPs from 9 to 17 nm (FIG. 2 panels a-c).

Preferably, said filling percentage of the reactor is between 40 and 60 vol. %.

The step of heating the reactor in point iv) is preferably carried out by inserting said sealed reactor into a pre-heated furnace at the solvothermal reaction temperature.

The reaction temperature is preferably between 180 and 240° C.

The reactor is preferably held at the reaction temperature for between 3 and 8 hours.

In a preferred embodiment, the ferrite nanoparticles obtained according to the method of the present invention are transferred to water by means of standard water transfer protocol (ligand-exchange or polymer wrapping).

As is known in the above-cited document WO 2013/150496, for example, in order to facilitate the transfer of nanoparticles to the required final use solvents, the nanoparticles may be functionalized with suitable ligands. Advantageously, the nanoparticles obtained according to the method described above readily lend themselves to being subjected to a variety of ligand-exchange methods or to methods of polymeric covering on the surface, obtaining nanoparticle water transfer yield close to 100% and stable dispersions even in the long term.

The ligand exchange may advantageously be carried out using tetramethylammonium hydroxide, polyethylene glycol and derivatives thereof. Examples of polyethylene glycol derivatives are gallol polyethylene glycol (gallolPEG) and α-nitrodopamine-o-carboxypoly(ethylene glycol).

The polymeric covering may advantageously be carried out using an amphiphilic polyanhydride. Examples of amphiphilic polyanhydrides are poly(maleic anhydride-alt-1-octadecene), poly(maleic anhydride-alt-1-tetradecene), poly(maleic anhydride-polyisobutylene). Alternatively, the MNPs obtained according to the method of the present invention may be also subjected to functionalization with a radical polymerization initiator for a monomer or comonomers susceptible to forming a thermoresponsive or pH-responsive polymer.

The method described herein is suitable for the large-scale preparation of nanoparticles for use in magnetic hyperthermia, with numerous advantages. In particular, said method makes it possible to obtain high yields of magnetic nanoparticles, while simultaneously maintaining a high level of control of the dimensions, size and size dispersion and colloidal properties of the end product, as well as outstanding heating performances. More specifically, the method described here has obvious advantages over the thermal decomposition synthesis methods, since it allows to prepare gram scale materials versus the tens of mg scale production of thermal decomposition method; it does not require operating in an atmosphere devoid of oxygen and under magnetic agitation, thereby substantially reducing the times and costs of the entire production process. Furthermore, the thermal profile of the method developed here is more direct and simpler; it in fact consists of just one heating step to temperatures below those used in the known thermal decomposition methods and reduced reaction times. With respect to the solvothermal synthesis methods, the method described here makes it possible to obtain nanoparticles having a greater degree of crystalline purity, reduced dimensions and lower polydispersity, consequently having better magnetic and colloidal properties.

The following examples are provided by way of illustration only.

EXAMPLES

Example 1: Synthesis of Ferrite Nanoparticles Using Aliphatic Aldehydes: Heptanal 8 mL (equal to 51 mmol) of 1-octanol (anhydrous, ≥99% Sigma-Aldrich), 0.2 g (equal to 0.8 mmol) of hexadecylamine (HDA, 98%, Sigma-Aldrich) and 0.6 mL (equal to 1.9 mmol) of oleic acid (OA, ≥99%, GC, Sigma-Aldrich) were brought into a homogenous solution in a two-neck round-bottom flask (25 mL, with an opening for the insertion of a thermocouple) at 60° C. using a heating jacket (the temperature is simply monitored, but a specific ramp is not applied) for 30 minutes with magnetic agitation (1100 rpm). No condensing units are required, no specific pressure and the dissolution was carried out under atmospheric pressure. After this, the solution was left to cool down to room temperature (RT) naturally. 2 mL (equal to 14.8 mmol) of iron pentacarbonyl (Sigma-Aldrich, >99.99%, purity in terms of metal traces) were then added at room temperature with magnetic agitation (1100 rpm). After 30 minutes, 1.4 mL of heptanal (Sigma-Aldrich, ReagentPlus®, ≥99%) was added as the directing agent. After 30 minutes, the solution was transferred to a Teflon-lined 25-mL autoclave that is filled up to 46.4 vol. % and is sealed in a stainless-steel jacket. The reactor was introduced into a furnace pre-heated to 200° C. and maintained for 6 hours, where the sample was subjected to the solvothermal crystallization process. No type of magnetic agitation was applied during the solvothermal reaction in order to prevent the possible aggregation of the nanoparticles formed, which may happen due to the magnetic characteristics of the product. The pressure inside the reactor may reach values of between 1.2 and 60 bar. For example, the pressure reached inside a Parr® reactor (Series 4560, 100 mL) was measured reaching values of between 20 and 60 bar during the reaction. At the end of the solvothermal reaction in the furnace, the reactor was left to cool down to room temperature naturally. The contents of the autoclave were then transferred to two 45-mL Falcon™ tubes with the aid of chloroform up to a volume of 15 mL. The Falcon™ tubes were subjected to ultrasound for 2 minutes, 30 mL of acetone were added, were briefly agitated and were subjected to centrifugation (4500 rpm for 20 min). After this, the supernatant was discarded and the product deposited in the Falcon™ tube was dispersed in 10 mL of chloroform in each tube for the subsequent characterization processes. See FIG. 1 for a summary of the general process used.

The nanoparticles obtained in this way were characterized by means of transmission electron microscopy (TEM). The results shown in FIG. 2*a* show the presence of spherical shapes and a dimensional distribution centered on 9±1 nm was obtained.

Example 2: Study of Size Tuning of the Ferrite Nanoparticles Using the Heptanal To obtain nanoparticles at different sizes, it was followed the procedure in the Example 1, and two experimental conditions (only reaction temperature and/or percentage filling of the autoclave) were changed. In the first case, the amounts of the chemicals were kept exactly as in Example 1, but the temperature of the furnace was set to 220° C. rather than from 200° C. as in Example 1. In the second case, the amounts of the chemicals were kept exactly as in Example 1, the temperature was kept at 200° C. but the final filling percentage of the autoclave of 25 mL, was set to 46.4% in volume. Alternatively, the, the amounts of the chemicals were kept exactly as in Example 1, the temperature was set at 220° C. and the autoclave filling percentage was set at 60% in volume.

The results of the TEM characterization shown in FIG. 2b show that increasing only the temperature (220° C.) there was an increase of the size from 9±1 to 13±2 nm and in the FIG. 2c it is possible to observe a further increase of the size (17±2 nm) using the combination of the higher temperature and higher final filling percentage of the autoclave of 25 mL (60% in vol).

Example 3: Synthesis of Ferrite Nanoparticles Using Other Aliphatic Aldehydes: Pentanal, Decanal and (Z)-hept-4-enal Following the same protocol described in the Example 1, more reactions were carried out using different aliphatic aldehydes as directing agents: pentanal, the decanal and the (Z)-hept-4-enal. The amounts of each of the aldehyde used for each the synthesis (in replacement to the heptanal of the Example 1) are summarized in Table 1.

TABLE 1

| Amount of the aliphatic aldehydes used for the synthesis of the ferrite nanoparticles. | |
| --- | --- |
| Pentanal | 1.0 mL (9.8 mmol) |
| Decanal | 1.8 mL (9.8 mmol) |
| (Z)-hept-4-enal | 1.3 mL (9.8 mmol) |

The TEM images results are shown in FIG. 2d-2f. FIG. 2d show the presence of nano-faceted and a dimensional distribution centered on 15±1 nm was obtained when using pentanal as directing agent. In FIG. 2e it is possible to observe the nano-faceted obtained using the decanal, with a dimensional distribution centered on 18±2 nm. FIG. 2f shows the TEM images of the nano-spheres obtained using the (Z)-hept-4-enal, with a dimensional distribution centered on 14±1 nm.

Example 4: Synthesis of Ferrite Nanoparticles Using Aromatic Aldehydes: 2-phenylacetaldehyde, 3-phenylpropanal and (E)-3-phenylprop-2-enal 3-phenylpropanal and (E)-3-phenylprop-2-enal The procedure described in the Example 1 it was followed, replacing the heptanal with 2-aldehydes having a $R_1$ saturated carbon chain bearing a phenyl group as sole substitute, at least in position C2 starting from the carbonyl group (See the TEM example of 2-phenylacetaldehyde and 3-phenylpropanal).

Alternatively, the inventors used unsaturated aldehydes bearing a phenyl group as substitute, at least in position C3 with respect to the carbonyl group (See the TEM example (E)-3-phenylprop-2-enal). The amounts of each of the aldehydes used in the synthesis are summarized in Table 2.

TABLE 2

| Amount of the 2-phenylacetaldehyde, 3 phenylpropanal, (E)-3-phenylprop-2-enal used in each of the synthesis of the ferrite nanoparticles. | |
| --- | --- |
| 2-phenylacetaldehyde | 1.2 mL (9.8 mmol) |
| 3-phenylpropanal | 1.3 mL (9.8 mmol) |
| (E)-3-phenylprop-2-enal | 1.2 mL (9.8 mmol) |

Figure 3:
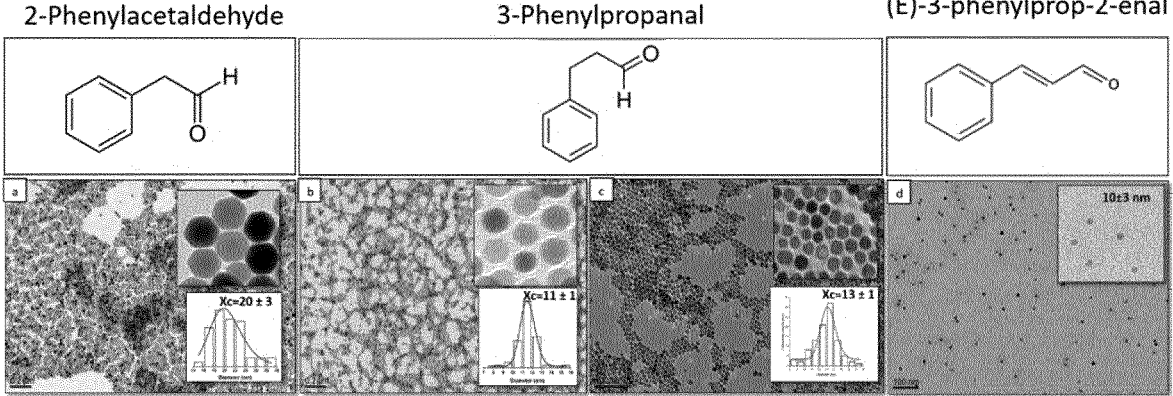
FIG. 3 shows the TEM images of MNPs obtained using different aromatic aldehydes of Formula (I) as the directing agents, i.e.: a) 2-phenylacetaldehyde, b) 3-phenylpropanal, c) (E)-3-phenylprop-2-enal.

The TEM results shown in FIG. 3a show the presence of the nano-faceted and a dimensional distribution centered on 20±3 nm was using 2-phenylacetaldehyde as directing agent. In FIG. 3b the TEM images of the nano-spheres obtained using the 3-phenylpropanal, with a size centered in 11±1 nm, are shown. Finally, in FIG. 3d it is possible to observe the nano-spheres obtained using the (E)-3-phenyl-prop-2-enal with a size of 10±3 nm.

Example 5: Study of the Control of the Size of Ferrite Nanoparticles Using the 3-Phenylpropanal To increase the size of the nanoparticles obtained with 3-phenylpropanal (Example 4), procedure of example 4 was followed with the only change on the temperature of the furnace that was set to 220° C. rather than 200° C. of example 4) and the final filling percentage of the autoclave of 25 mL was set to 60% in vol (rather than 46.4%)) were changed (See FIG. 3c, the TEM size of the MNPs increases from 11±1 to 13±1 nm).

Example 6: Synthesis of Ferrite Nanoparticles Using Different Ketones: Trans-1-Phenyl-2-buten-one, methyl phenyl ketone and diphenyl ketone For the synthesis with ketones, the procedure described in the Example 1 was identical with the sole difference that the heptanal was replaced with each of the chosen ketone.

The examples of ketones used include trans-1-phenyl-2-buten-one, methyl phenyl ketone and diphenyl ketone. The amount of ketones used in the synthesis are summarized in Table 3.

TABLE 3

| Amount of the trans-1-phenyl-2-buten-one, methyl phenyl ketone and diphenyl ketone used for the synthesis of ferrite nanoparticles. | |
| --- | --- |
| Trans-1-phenyl-2-buten-one | 1.5 mL (9.8 mmol) |
| Methyl Phenyl Ketone | 1.4 mL (9.8 mmol) |
| Diphenyl Ketone | 1.6 mL (9.8 mmol) |

With diphenyl ketone, two different experiments were conducted at two different temperature. In particular, the protocol followed was identical to the Example 1 with the only difference that diphenyl ketone was replacing the epthanal and in a first synthesis the temperature of the furnace was set at 200° C. while in the second synthesis the temperature of the furnace was set at 240° C.

Figure 4:
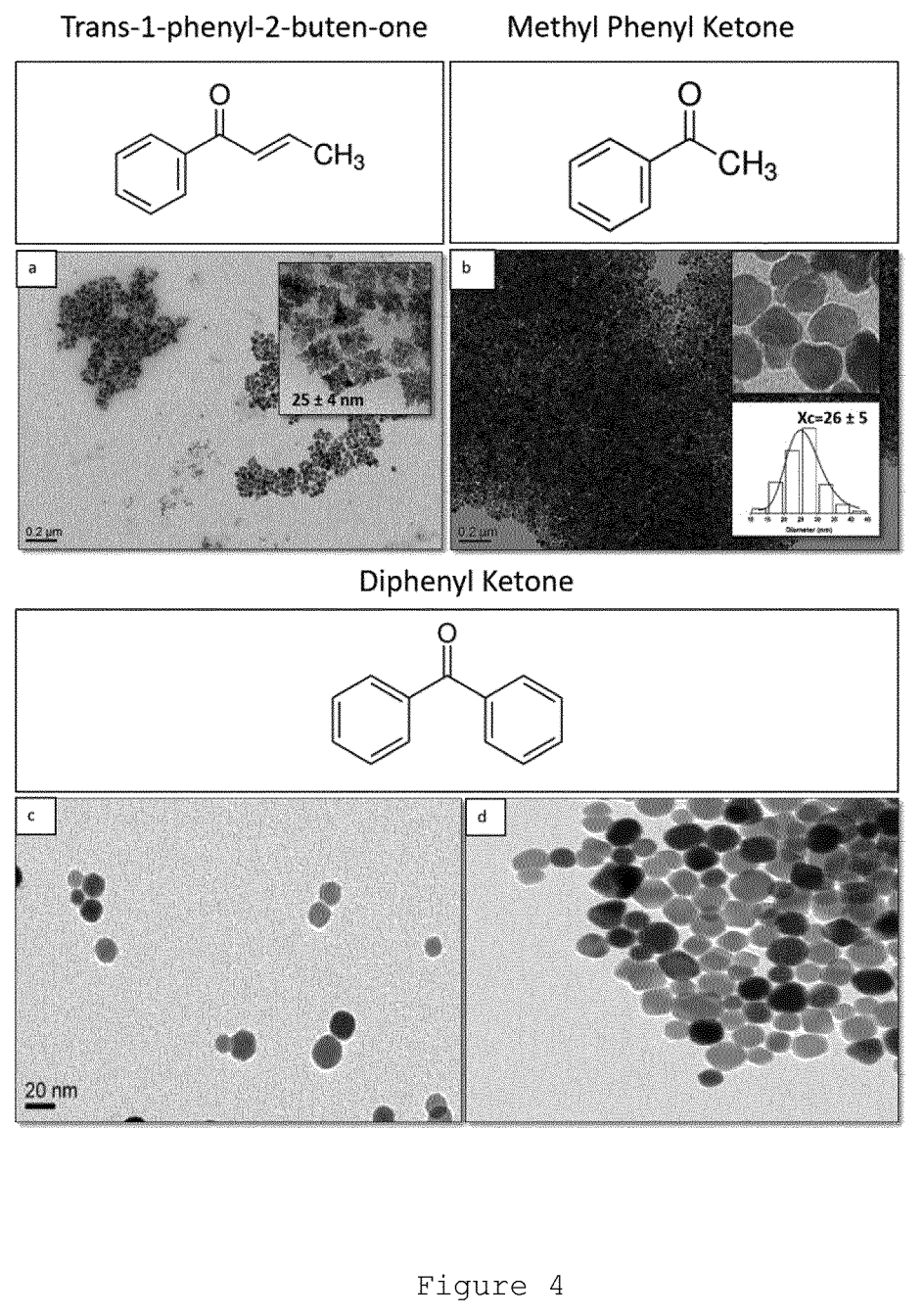

The TEM images of the MNPs obtained with the ketones are shown in FIG. 4.

With trans-1-phenyl-2-buten-one (FIG. 4a) a flower-like shape with an overall dimension of 25±4 nm are obtained. With methyl phenyl ketone (FIG. 4b), the nanoparticles present a so called "mushroom-like" shape, which is an anisotropic shape with a part that is thicker (like the cap of a mushroom) and a part that is narrower (like the stipe, or the base of a mushroom).

With biphenyl ketone (FIG. 4c reaction at 200° C. and 4d reaction at 240° C.), the nanoparticles obtained are a sort of faceted nanoparticles with the dimension included in a range of 16-25 nm.

Example 7: Ligand Exchange Protocol for Water Transfer and Comparative Study of the Colloidal Properties For this experiment, magnetite nanoparticles having average size of 20±3 nm (sample chosen is Example 4 prepared with 2-phenylacetaldhyde), tetramethylammonium gallol polyethylene glycol (abbreviated as GA-PEG) or tetramethylammonium hydroxide (abbreviated as TMAOH) were used as water transfer ligands.

To carry out the ligand exchange with GA-PEG, 20 mL of a chloroform solution containing MNPs (MNPs concentration at [Fe]=1 mg/mL) were added to 11.7 mL of GA-PEG solution (0.1 M in chloroform containing 1.1 mL of triethylamine) and mechanically agitated overnight in an orbital agitator at room temperature. The mixture was then transferred to a separating funnel and the MNPs were transferred in a liquid phase by means of liquid-liquid extraction using water/toluene. The solution was concentrated up to 10 mL under reduced pressure conditions at 50° C. First, in a tube cellulose membrane (molecular weight cut-off of 50 kDa) the 10 mL sample was dialysed against 5 L of deionized water for two days changing the water every 5 hours. Lastly, the recovered MNPs solution was concentrated to ca. 1.5 mL with centrifugal filter (molecular weight cut off of 100 kDa).

For the samples synthetized in the Example 1-4, the ligand-exchange protocol using TMAOH was applied (Langmuir 2010, 26(8), 5843-5847). This is a short ligand that may replace the organic surfactant on the surface of the nanoparticles, providing a negative charge having a physiological pH that are able to improve the stability by charge repulsion. For the ligand-exchange process, 200 molecules of TMAOH per each square nanometer of nanoparticle surface is added.

For a typical example of TMAOH protocol, 1 mL of MNPs (having a MNP concentration between 3-5 mg/mL in Fe prepared accordingly to example 5) is collected in a glass vial. 5 mL of acetone are then added and centrifugation at 4500 rpm for 20 minutes was performed. After discarding the supernatants, the pellet was gently air-dried and 1 mL of ethanol solution, containing 50 mg of TMAOH, was added. The solution was treated in a ultrasonicator for 30 minutes at room temperature. Next 5 mL of water was added to the solution and the ethanol/water solvent was then exchanged with pure water using an Amicon® centrifugal filter (100-K MWCO). At least 6 cycles of Amicon filtration were needed to ensure that the ethanol is discarded. The final volume of the sample collected is around 1 mL (3-6 mg/mL of Fe).

Figure 5:
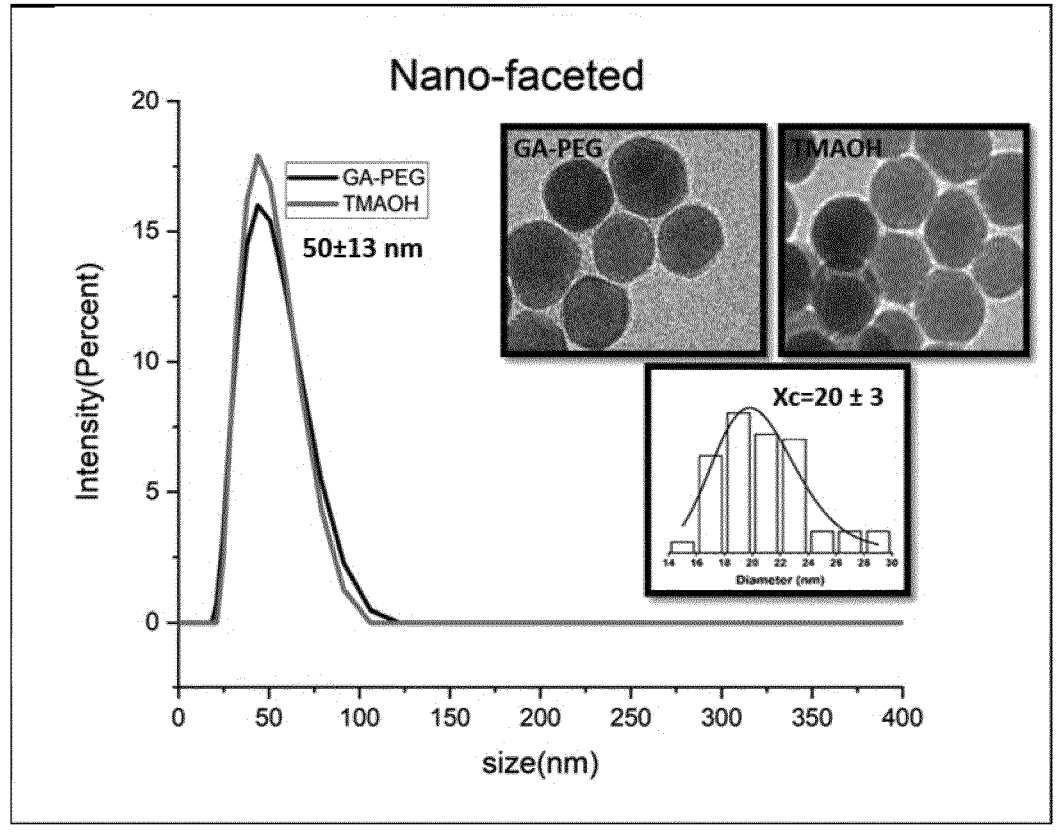
FIG. 5 shows examples of hydrodynamic size distribution curves measured by Dynamic Light Scattering (DLS) of aqueous solution of nano-faceted particles stabilized with GA-PEG (black) or TMAOH (red). Insets show TEM images of the GA-PEG and TMAOH MNPs and size distribution of the magnetic core determined through TEM image (20±3 nm).

Hydrodynamic curves for GA-PEG and TMAOH stabilized nano-faceted nanoparticles showed as an example in FIG. 5, having mono-modal hydrodynamic sizes confirm the stability of this MNPs in water (FIG. 5). The average hydrodynamic size in water is of approximately 50 nm, which is definitely higher than to the magnetic core size as determined by TEM, due to the hydrodynamic polymer shell (either repulsive forces for TMAOH or to the steric hindrance due to the GA-PEG).

Example 8: Comparative Study of the Magnetic Performance

To demonstrate the potential of the MNPs obtained through this method as heat mediators in MH treatment, the Specific Absorption Rate (SAR) values of MNPs prepared accordingly to Example 2 (heptanal at 220° C. and 60% in vol filling percentage), Examples 3 (pentanal, decanal and (Z)-hept-4-enal) and Example 4 (2-phenylacetaldehyde) were measured. For the calorimetric measurement, under well-defined radiofrequency conditions (well-defined frequency, f, and field amplitude, H, values), the temperature versus time curve were recorded when switching on the AC field on a sample volume of 0.3 mL and at an iron concentration of 1-6 mg/mL, to guarantee close-to-adiabatic conditions. AC magnetic field at frequencies of 105 kHz, or 220 kHz or 300 kHz and magnetic field amplitudes of 12, or 16 or 24 kAm$^{-1}$ were applied. All measurements were performed in water ($C_{water}$=4185 JL$^{-1}$K$^{-1}$). The reported SAR values was calculated accordingly to the formula:

$$SAR\left(W/g_{Fe}\right) = \frac{m_d \times C}{m_{Fe}} \frac{dT}{dt}$$

Where: C is the specific heat capacity of water (4.18 J g$^{-1}$ K$^{-1}$); $m_{Fe}$ is the iron mass per g of dispersion; $m_d$ is the mass of the dispersion.

Figure 6:
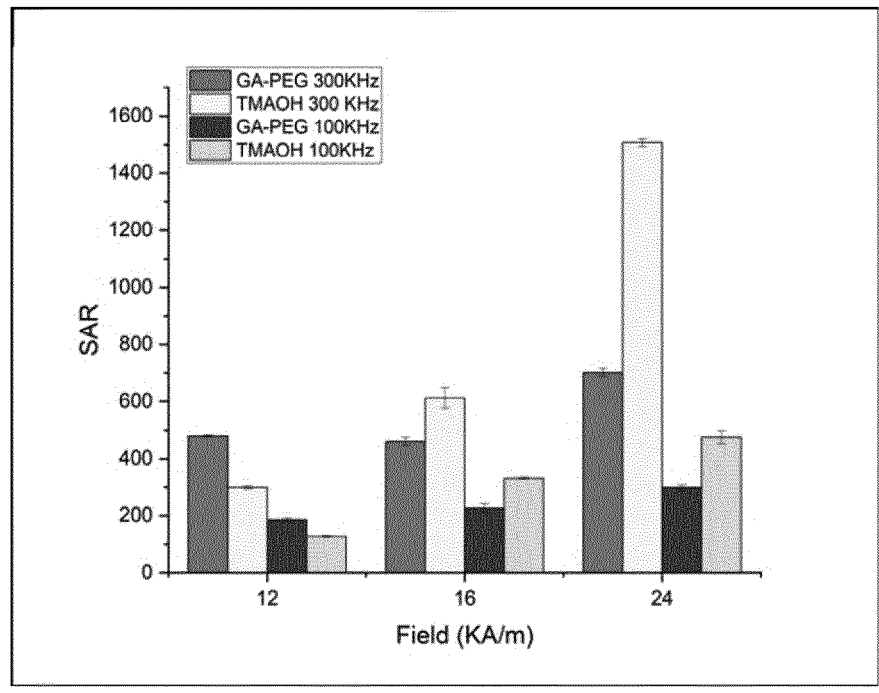
FIG. 6 shows the SAR analysis at different field conditions (H=12-24 kA/m and f=100-300 kHz) of the 20±3 nm particles synthetized with 2-phenylacetaldehyde as the directing agent and transferred to water with gallol polyethylene glycole (GA-PEG) and tetra-methyl ammonium hydroxide (TMAOH), showing the outstanding colloidal MH heat performances of the MNPs thereby obtained.
Figure 7:
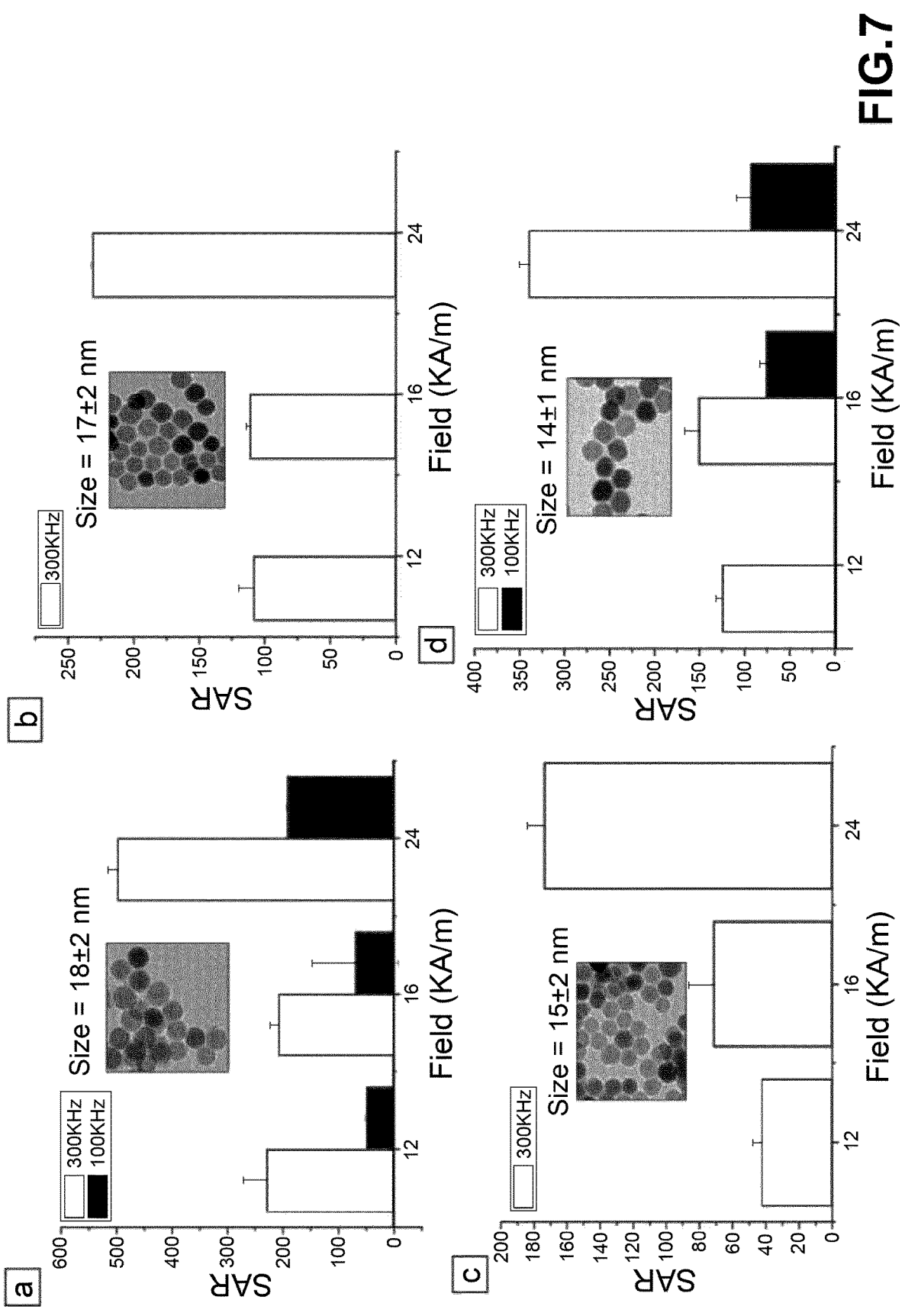
FIG. 7 shows a SAR analysis at different fields amplitudes and frequencies (H=12-24 kA/m and f=100 or 300 kHz) of TMAOH water stabilized MNPs obtained by different examples and having sizes below 20 nm. a) 18±2 nm Nano-faceted particles synthetized with the decanal, b) 17±2 nm Nano-faceted particles synthetized with the heptanal, c) 15±2 nm and d) 14±2 nano-faceted particles synthetized with the pentanal.

Each SAR value is the mean of four measurements Only the first seconds of the $\Delta T/\Delta t$ curve were used to calculate the slope of the curve thus the SAR values (FIG. 6 and FIG. 7). The heating properties of the ferrite nanoparticles obtained according to the invention were reported and compared with: i) nano-faceted particles of similar size; ii) nano-spherical particles of similar size prepared according to high temperature thermal decomposition synthesis route (G. Salas et al. J. Mater. Chem., 2012, 22, 21065-2107) (through), and iii) with a commercially available product, Resovist®, whose heating performance has been reported by Darwish, M. et al. (Nanomaterials 9.8 (2019): 1176). For the comparison of SAR values see FIG. 8.

First, the heating performance of nano-faceted particles obtained according to Example 4 with a size distribution of 20±3 nm and stabilized in aqueous media with both GA-PEG and TMAOH molecules (FIG. 6) at 300 and 100 kHz frequency and different field amplitude is reported. This shape has outstanding SAR values (for H=24 kA/m and f=300 kHz) of up to 780 and 1500 W/g$_{Fe}$ for GA-PEG and TMAOH-NPs (FIG. 6), respectively. Indeed, some authors like Mehdaoui et al. have found that the optimal diameter of magnetite NPs for MH applications (for field conditions close to those used in clinics) is 20 nm, which is precisely the size of the nano-faceted MNPs obtained by the present invention. This size indeed lies in the barrier of the transition from superparamagnetic to ferrimagnetic regime. As expected, when comparing the performances of MNPs below the optimal size of 20 nm have lower heating Performance. Nano-faceted particles of 18±2 nm have SAR values of up to 200-500 W/g$_{Fe}$ with field conditions of 300 kHz and 24 kA/m, respectively (FIG. 7a). For even smaller sizes like for 17±2, 15±2 and 14±1 nm, the SAR values decrease down to 180-350 W/g$_{Fe}$ with for the same field conditions of 300 kHz and 24 kA/m, as shown in FIG. 7b-c. SAR values at 100 kHz are definitely lower than that at 300 kHz but still significant (FIGS. 7a and 7d) A comparison between the heating performances of the MNPs obtained by the present invention with those of similar size and morphology produced by thermal decomposition as in the prior art (G. Salas et al. J. Mater. Chem, 2012, vol. 22, no 39, p. 21065-21075) (FIG. 8), the MNPs obtained by the present invention have SAR values which are at least 2 times higher than the corresponding ones of similar size obtained by the prior art method. G. Salas et a., 2012 report SAR values of 50 W/g$_{Fe}$ for MNPs with a size of 14±1 nm and 90 W/g$_{Fe}$ for MNPs with a size of 18±2 nm at H=32 kA/m and f=77 kHz (Hf=2.4×10$^9$ A/ms) and for the same size/size distribution and morphology, the present invention provides 100 and 200 W/g$_{Fe}$e at H=24 kA/m and f=100 kHz, and same Hf product (Hf=2.4×10$^9$ A/ms).

In fact, the best sample (size of 22±2 nm) in G. Salas et al., 2012 has SAR values of 200 W/g$_{Fe}$ while the sample of similar size (20±3 nm) obtained with the method of the invention has SAR values of 475 W/g$_{Fe}$. Finally, some of the samples obtained by the present invention are hard to compare to those reported in the literature because of the AC field conditions used, which are slightly different in some cases. For instance, nano-spheres of 17±2 nm produced with the method of the present invention are capable of heating the same than those of similar size produced by thermal decomposition, but in the method of the present invention at milder conditions of AC field are used.

Significantly, in a comparison between the MNPs obtained by the present invention and a commercially available product, Resovist®, the SAR value for Resovist reported in the literature is approximately 25 W/g$_{Fe}$ (Darwish, M. et al., Nanomaterials 9.8 (2019): 1176) while the SAR value obtained by the present invention is ca. 20 times higher at similar field conditions (105 kHz and H=40 kA/m and Hf factor of 4.2×109 A/Ms for Resovist® versus 100 kHz and 24 kA/m and Hf factor of 2.9×10$^9$ A/Ms for MNPs obtained with the present invention) (FIG. 8).

The data in FIGS. 6-8, show that the SAR values measured for all the ferrites obtained according to the present invention are suitable for clinical application.

Example 9: Mass of Ferrite Nanoparticles Obtained in a Parallelized Way

Advantageously, the method of the present invention was scaled-up by performing parallel reactions, which means that multiple vessels are placed in the oven (for example up to 10). With the method of the invention, it is therefore possible to achieve gram-scaled amounts of high quality MNPs at different size and having outstanding heating performances in one single oven cycle (see the exact mass produced in the case of each shape in Table 4). Also, besides placing more reactions in parallel per each cycle, given the short duration of each reaction cycle (from 3 to 8 h), these amounts can be further scaled by increasing the number of cycles to be performed per day. Table 4 summarizes the mass of the MNPs obtained for the different examples obtained at 200° C., with the 25 mL-autoclave, considering that 10 synthesis were conducted in parallel.

TABLE 4

| Ligand used in the synthesis | Mass of MNPs (g) |
|---|---|
| Heptanal | 1 |
| Pentanal | 1 |
| Decanal | 1 |
| (z)-hept-4-enal | 2 |
| 2-phenylacetaldehyde | 5 |
| 3-phenylpropanal | 1 |
| Methyl Phenyl ketone | 1 |

Thus, the solvothermal approach of the present invention, which uses aliphatic/aromatic aldehydes or ketones as shape directing agents in the synthesis reaction, leads to gram scaled production of MNPs having superior structural and magnetic features, which even surpass the heat performances of very similar MNPs but produced by high temperature thermal decomposition methods.

What is claimed is:

1. A method for preparing ferrite nanoparticles having a Specific Absorption Rate (SAR) of at least 100 W/gFe at a frequency of 100 kHz and a magnetic field of 24 kA/m, the method comprising the following steps:
   i) providing a solution comprising a fatty acid, an aliphatic amine, and an alcoholic solvent;
   ii) adding to the solution a directing agent and at least one organometallic precursor compound comprising Fe and optionally a second organometallic precursor compound comprising a metal selected from Mn, Co, Zn, thereby obtaining a reaction mixture;
   iii) transferring the reaction mixture to a sealed reactor, thereby obtaining a filling percentage thereof of between 20 and 70 vol. %; and
   iv) heating said sealed reactor to a temperature ranging between 180° C. and 240° C. for a duration of between 3 and 8 hours,
   wherein the directing agent is an aldehyde or ketone of Formula (I):

$$R_1—(C=O)R_2 \hspace{3cm} \text{Formula (I)}$$

wherein R$_1$ is a linear or branched, saturated or unsaturated carbon chain having a length of from 1 to 13 carbon atoms, optionally substituted with an aromatic substituent, and
   R$_2$ is selected from the group consisting of hydrogen, an aromatic ring and a linear or branched, saturated or unsaturated carbon chain having a length of from 1 to 10 carbon atoms,
   with the provisos that:
   when R$_2$ is hydrogen and R$_1$ is an unsaturated carbon chain substituted with an aromatic substituent, the aromatic substituent is located at position 3 or higher with respect to the carbonyl group —(C=O), or
   when R$_2$ is hydrogen and R$_1$ is a saturated carbon chain substituted with an aromatic substituent, the aromatic substituent is located at position 2 or higher with respect to the carbonyl group —(C=O), with the further proviso that when the aromatic substituent is located at position 2, the aromatic substituent is the sole substituent at position 2.

2. The method of claim 1, wherein the aromatic substituent in the definition of R$_1$ is a phenyl group optionally bearing one or more substituents.

3. The method of claim 1, wherein the aromatic substituent in the definition of R$_2$ is a phenyl group optionally bearing one or more substituents.

4. The method of claim 1, wherein R1 is carbon chain having a length of from 1 to 11 carbon atoms.

5. The method of claim 1, wherein R2 is carbon chain having a length of from 1 to 5 carbon atoms.

6. The method of claim 1, wherein the directing agent of Formula (I) is selected from the group consisting of pentanal, heptanal, decanal, 3-phenylpropanal, 2- phenylacetaldehyde, (Z)-hept-4-enal, (E)-3-phenylprop-2-enal, trans-1-phenyl-2-buten-one, methyl phenyl ketone and diphenyl ketone.

7. The method of claim 1, wherein said aliphatic amine in step i) is an alkyl amine.

8. The method of claim 1, wherein said fatty acid is a saturated or unsaturated fatty acid having an aliphatic chain with a length of between 10 and 18 carbon atoms.

9. The method of claim 1, wherein said alcoholic solvent is selected from the linear alcohols having an alkyl chain of between 2 and 8 carbon atoms.

10. The method of claim 1, wherein said organometallic precursor compound is selected from the group consisting of iron pentacarbonyl of formula $Fe(CO)_5$, zinc acetylacetonate of formula $Zn(AcAc)_2$, cobalt acetylacetonate of formula $Co(AcAc)_2$, manganese (II) acetylacetonate of formula $Mn(AcAc)_2$, and mixtures thereof.

11. The method of claim 1, wherein said filling percentage is between 40 and 70 vol. %.

12. The method of claim 1, wherein the ferrite nanoparticles obtained are transferred to water by means of a ligand-exchange step or a polymeric covering step.

13. The method of claim 12, wherein ligands used in said ligand-exchange step are selected from the group consisting of tetramethylammonium hydroxide, polyethylene glycol and derivatives thereof.

\* \* \* \* \*